United States Patent
Hu et al.

(10) Patent No.: US 9,022,943 B2
(45) Date of Patent: May 5, 2015

(54) METHOD FOR DETECTING VASCULAR SCLEROSIS

(75) Inventors: Wei-Chih Hu, Chung Li (TW); Liang-Yu Shyu, Chung Li (TW); Yuan-Ta Shih, Chung Li (TW); Yi-Jung Sun, Chung Li (TW); Chen-Huan Chen, Taipei (TW); Hao-Min Cheng, Taipei (TW)

(73) Assignee: Chung Yuan Christian University, Chung Li (TW)

( * ) Notice: Subject to any disclaimer, the term of this patent is extended or adjusted under 35 U.S.C. 154(b) by 911 days.

(21) Appl. No.: 12/716,585

(22) Filed: Mar. 3, 2010

(65) Prior Publication Data

US 2011/0071408 A1   Mar. 24, 2011

(30) Foreign Application Priority Data

Sep. 24, 2009   (TW) .............................. 98132206 A

(51) Int. Cl.
*A61B 5/02*   (2006.01)
*A61B 5/022*   (2006.01)

(52) U.S. Cl.
CPC ............. *A61B 5/022* (2013.01); *A61B 5/02007* (2013.01); *A61B 5/02233* (2013.01)

(58) Field of Classification Search
CPC .......... A61B 5/02; A61B 5/021; A61B 5/022; A61B 5/0225
USPC .................................. 600/301, 481, 490–500
See application file for complete search history.

(56) References Cited

U.S. PATENT DOCUMENTS

| | | | | |
|---|---|---|---|---|
| 4,328,810 A | * | 5/1982 | Hill et al. ....................... | 600/493 |
| 4,427,013 A | * | 1/1984 | Nunn et al. .................... | 600/494 |
| 5,211,177 A | * | 5/1993 | Chesney et al. ............... | 600/485 |
| 2003/0060720 A1 | * | 3/2003 | Lee et al. ....................... | 600/490 |
| 2004/0254485 A1 | * | 12/2004 | Wu et al. ....................... | 600/490 |

* cited by examiner

*Primary Examiner* — Jacqueline Cheng
*Assistant Examiner* — Puya Agahi
(74) *Attorney, Agent, or Firm* — Rosenberg, Klein & Lee

(57) ABSTRACT

A method for detecting vascular sclerosis is revealed. Firstly set a cuff on a human hand. Then inflate the cuff and later deflate the cuff. Next measure a pressure of the cuff and generate a pressure sensing signal. Process the pressure sensing signal to generate a processed signal and convert the processed signal. Then calculate a systolic pressure and a diastolic pressure according to the converted processed signal and also obtain a vasodilation constant. Thus a hardening of blood vessels is detected according to the vasodilation constant.

13 Claims, 4 Drawing Sheets

METHOD FOR DETECTING VASCULAR SCLEROSIS

BACKGROUND OF THE INVENTION

1. Field of Invention

The present invention relates to a detection method, especially to a method for detecting blood vessel hardening (vascular sclerosis).

2. Description of Related Art

Due to lives under high pressure and delicate foods, high blood pressure has become one of the ten leading causes of death. People not only have to monitor their blood pressure but also control the food intake for prevention of high blood pressure. In recent years, cardiovascular disease has also been one of the ten leading causes of death and has being with an increasing rate according to statistics of the department of health. The cardiovascular disease refers to arterial disease (atherosclerosis) so that a hardening of a blood vessel (vascular sclerosis) is one of important indicators of cardiovascular diseases. Once the hardening of blood vessels is discovered early, the cardiovascular disease can be prevented. Thus people got to monitor their blood pressure and the degree of blood vessel hardening so as to check their health conditions. Therefore, both high blood pressure and cardiovascular diseases can be prevented.

Along with increasing incomes, change of population structure, adoption of new medical technology, and some other factors, people have paid more attentions to health and medical and health devices such as blood pressure monitors, glucosemeters, etc., have been essentials for families. Thus it is convenient for users to measure their blood pressure and blood glucose so as to learn their health conditions for disease prevention. Although the medical technology is quite advanced now, there is still no easy way to measure the degree of blood vessel hardening, or an index of vascular stiffness. Thus there is no good measure of vascular stiffness assessment of health conditions. Therefore, cardiovascular disease remains one of the ten leading causes of death.

A conventional way of diagnosis is an intrusion-detection way. The procedures are not only complicated but also time-consuming. Thus the most common index of arterial stiffness adopted now is Pulse Wave Velocity (PWV). It measures the velocity of the blood pressure waveform between two sites and requires two sets of cuffs for measuring blood pressure as well as a single-lead ECG provides a time reference. The two sets of cuffs are arranged at the hand and the ankle respectively so as to obtain the time difference between the pulses of the two sites. Then by the distance between the two sites, the Pulse Wave Velocity is obtained. Generally, the normal PWV is less than 1200 mm/sec. The above way of measurement needs to measure many physiological parameters and the procedures are complicated. The design of the medical device for measurement is also complicated due to complicated procedures. Thus the detection of vascular stiffening is not so prevalent. Therefore, people are unable to monitor conditions and changes of the blood vessels for prevention of vascular diseases.

There is a need to develop a method for detecting vascular sclerosis that not only overcomes above shortcomings but also simplifies the processes.

SUMMARY OF THE INVENTION

Therefore it is a primary object of the present invention to provide a method for detecting vascular sclerosis that obtains a vasodilation constant by a systolic pressure and a diastolic pressure and check the vascular sclerosis according to the vasodilation constant. The systolic pressure and the diastolic pressure are calculated according to the pressure of a cuff.

It is another object of the present invention to provide a method for detecting vascular sclerosis that measures in a simple way and obtains a vasodilation constant at the time of measuring the systolic pressure and the diastolic pressure so as to check vascular sclerosis.

In order to achieve above objects, a method for detecting vascular sclerosis according to the present invention includes following steps. At first, set a cuff and inflate the cuff to make the cuff expand. Then deflate the cuff. During the deflation, measure a pressure of the cuff and generate a pressure sensing signal. Net process the pressure sensing signal to generate a processed signal and convert the processed signal. Calculate a systolic pressure and a diastolic pressure according to the converted processed signal and also obtain a vasodilation constant. Whether vascular stiffening occurs is checked according to the vasodilation constant. Thus the systolic pressure and the diastolic pressure are measured and the vasodilation constant is calculated according to the diastolic pressure so as to detect the vascular sclerosis.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
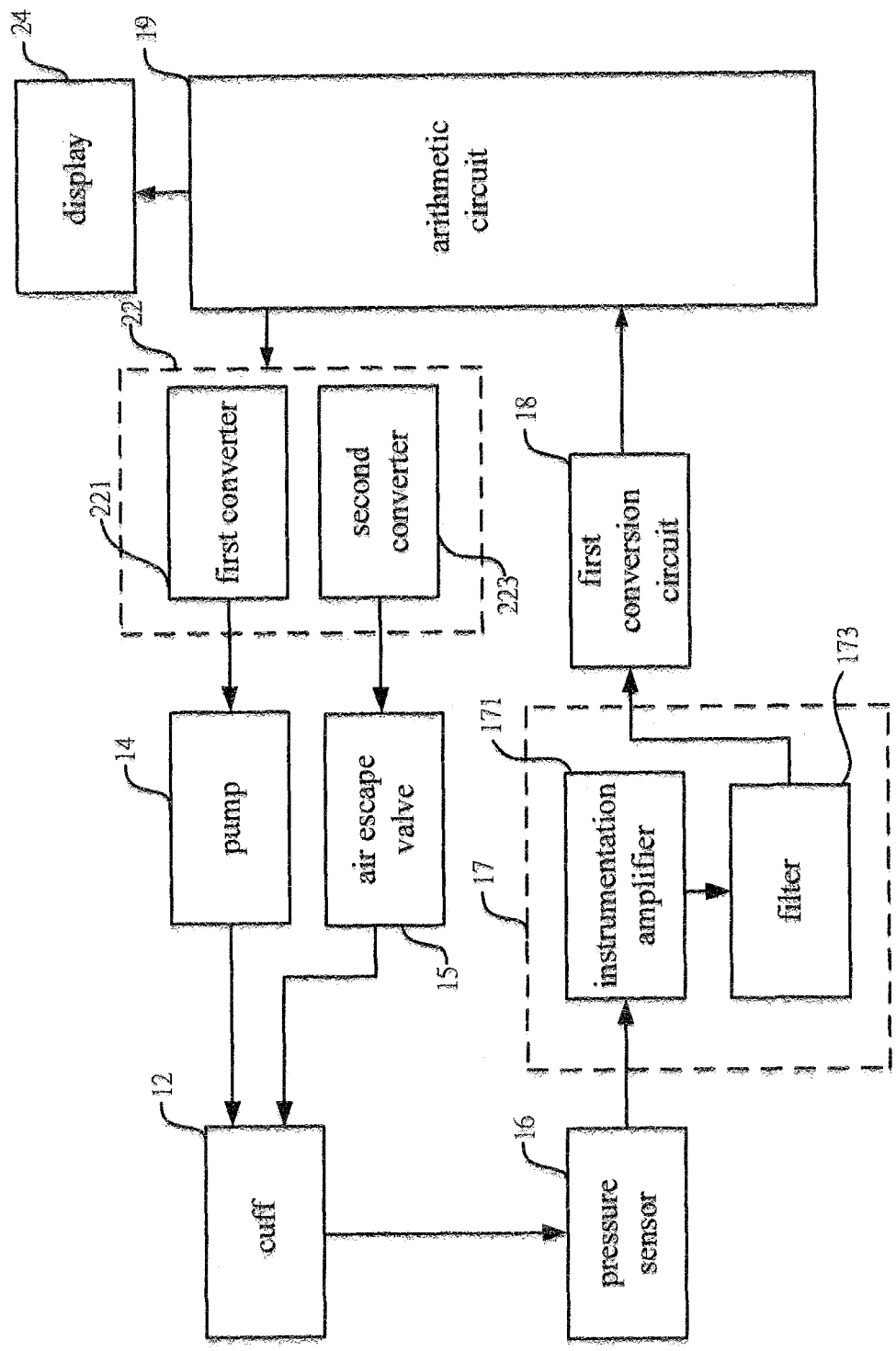
FIG. 1 is a block diagram of an embodiment of a blood pressure monitor that detects vascular sclerosis according to the present invention.

As shown in FIG. 1, a blood pressure monitor that detects vascular sclerosis according to the present invention includes a cuff 12, an air pump 14, an air escape valve 15, a pressure sensor 16, a processing circuit 17, a first conversion circuit 18, an arithmetic circuit 19, a second conversion circuit 22 and a display 24. The cuff 12 is wrapped around people's hands and is pumped up and inflated by the air pump 14 connected therewith. In this embodiment, the air pump 14 is an electric air pump that inflates the cuff 12 in a linear way. The air escape valve 15 is coupled with the air pump 14 so as to release air in the cuff 12. In this embodiment, the air escape valve 15 is an electric valve or a linear valve that releases air from the cuff 12 in a linear way.

Refer to FIG. 1, the pressure sensor 16 is disposed on the cuff 12 for measuring a pressure of the cuff 12 and generating a pressure sensing signal that is a waveform signal. The processing circuit 17 is coupled with the pressure sensor 16 to process the pressure sensing signal and generate a processed signal which is also a waveform signal. The processing circuit 17 mainly deals with the pressure sensing signal such as amplifying the waveform signals and filtering noises of the waveform signals for convenience of following processes such as conversion and calculation of the first conversion circuit 18 and the arithmetic circuit 19 so as to increase the accuracy. In an embodiment of the present invention, the processing circuit 17 is an analog processing circuit.

In this embodiment, the processing circuit 17 includes an instrumentation amplifier 171 and a filter 173. The instrumentation amplifier 171 is coupled with the pressure sensor 16 to amplify the pressure sensing signal while the filter 173 coupled with the instrumentation amplifier 171 is for filtering the amplified pressure sensing signal. If the noise-to-signal ratio is not high, the pressure sensing signal generated from the pressure sensor 16 is amplified by the instrumentation amplifier 171 and then is directly sent to the first conversion circuit 18, without disposition of the filter 173. The above embodiment is only a preferred embodiment of the present invention. The design of the instrumentation amplifier 171 varies according to different kinds of pressure sensors 16, the state of the pressure sensing signal or requirements of the arithmetic circuit 19.

Still refer to FIG. 1, the first conversion circuit 18 for conversion of the processed signal from an analog signal to a digital signal is coupled with the processing circuit 17. In an embodiment of the present invention, the first conversion circuit 18 is an analog-to-digital converter that samples waveform of the processed signal and outputs the sampled result which is a digital signal. The arithmetic circuit 19 coupled with the first conversion circuit 18 is used to receive the processed signal being converted by the first conversion circuit 18 and then calculate a systolic pressure, a diastolic pressure and a vasodilation constant of the user according to the received processed signal that represents a pressure change of the cuff 12. The systolic pressure and the diastolic pressure are indicators for checking blood pressure while the vasodilation constant is used to check whether the vascular sclerosis happens.

Moreover, the arithmetic circuit 19 is coupled with the display 24 so as to send the measured data of the systolic pressure, the diastolic pressure and the vasodilation constant to the display 24 for users to read. Furthermore, according to the received processed signal, the arithmetic circuit 19 obtains and sends an average blood pressure and a pulse rate to the display 24 for display. In this embodiment, the display 24 is a liquid crystal display (LCD).

In addition, the arithmetic circuit 19 generates an inflation control signal and a deflation control signal for control of the air pump 14 and the air escape valve 15 respectively. The arithmetic circuit 19 in this embodiment is a microprocessor. Once the air pump 14 and the air escape valve 15 can only receive analog signals, the second conversion circuit 22 of the present invention can convert both the inflation control signal and the deflation control signal generated from the arithmetic circuit 19 into analog signals, respectively sent to the air pump 14 and the air escape valve 15. Thus the air pump 14 is controlled to inflate the cuff 12 and the air escape valve 15 is controlled to release air from the cuff 12.

The second conversion circuit 22 consists of a first converter 221 and a second converter 223. In a preferred embodiment, the first converter 221 as well as the second converter 223 is a digital to analog converter. The first converter 221 is coupled between the arithmetic circuit 19 and the air pump 14 and is used for converting the inflation control signal generated by the arithmetic circuit 19 into an analog signal and sending the analog signal to the air pump 14 so as to control the air pump 14 for inflation of the cuff 12. The second converter 223 coupled between the arithmetic circuit 19 and the air escape valve 15 is for converting the deflation control signal generated by the arithmetic circuit 19 into an analog signal and sending the analog signal to the air escape valve 15 so as to control the air escape valve 15 for air releasing of the cuff 12.

Figure 2:
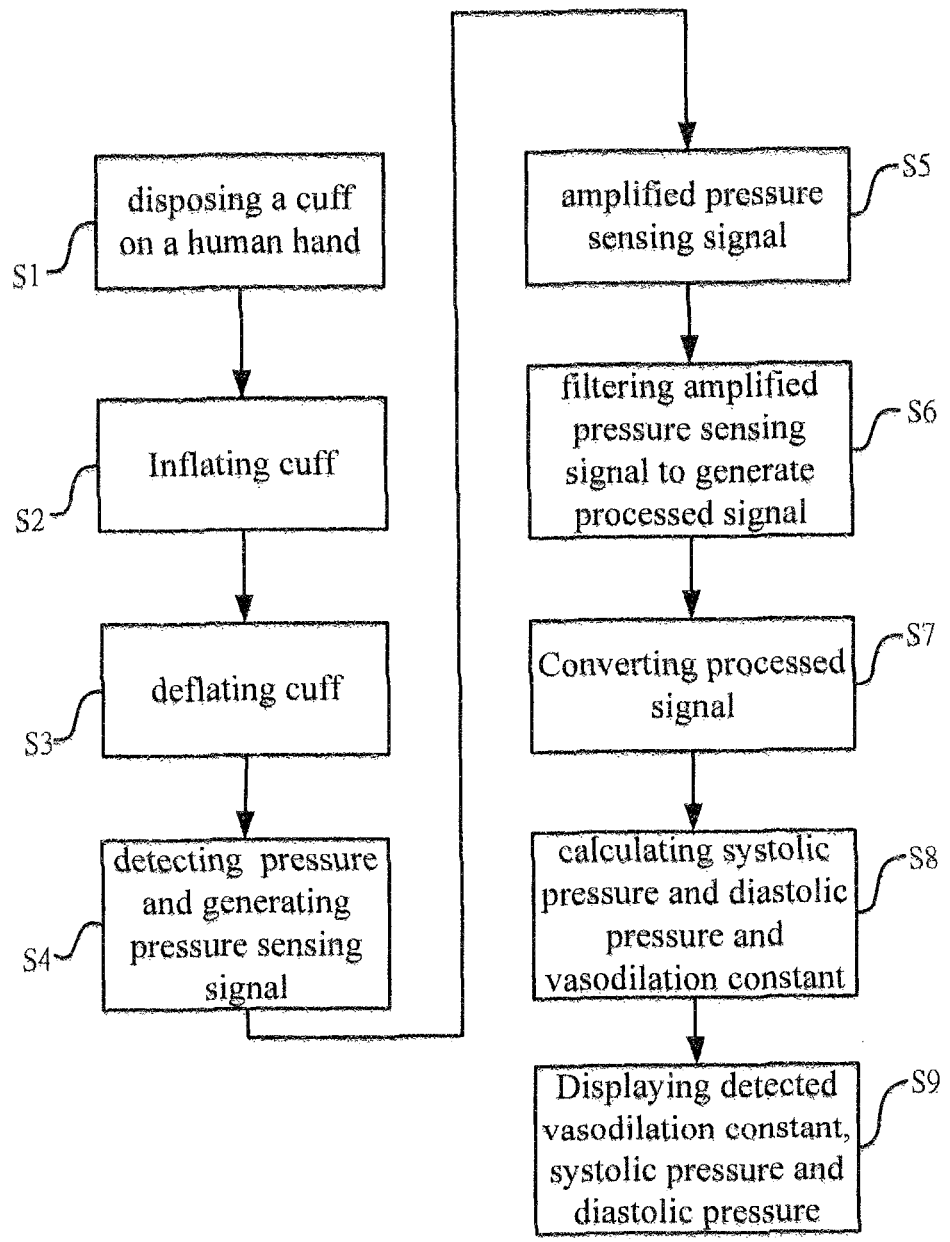
FIG. 2 is a flow chart of an embodiment of a method for detecting vascular sclerosis according to the present invention.

Refer to FIG. 2, a flow chart of a method for detecting vascular sclerosis according to the present invention is revealed. As shown in figure, firstly take the step S1, dispose a cuff 12 on a human hand. Then as shown in the step S2, the cuff 12 is inflated by the air pump 14 that receives an inflation control signal generated from the arithmetic circuit 19. The arithmetic circuit 19 controls the air pump 14 to inflate in a linear way. Later, as shown in the step S3, the arithmetic circuit 19 generates and sends a deflation control signal to the air escape valve 15 so as to control the air escape valve 15 that releases air from the cuff 12. Thus the gas pressure inside the cuff 12 is decreasing gradually. The arithmetic circuit 19 controls the air escape valve 15 to deflate in a linear way. Next, refer to the step S4, the pressure sensor 16 detects a pressure of the cuff 12 and generates a pressure sensing signal correspondingly. The pressure sensing signal is a waveform signal whose waveform oscillates along with the pulse beat.

Next the pressure sensing signal is processed so as to get the processed signal. As shown in the step S5 and the step S6, the pressure sensing signal is firstly amplified by the instrumentation amplifier 171 and then the amplified pressure sensing signal is filtered by the filter 173 so as to generate the processed signal. Then refer to the step S7, the processed signal is converted to a digital signal by the first conversion circuit 18. As shown in the step S8, the arithmetic circuit 19 calculates a systolic pressure and a diastolic pressure according to the converted processed signal and also calculates a vasodilation constant. Thus while measuring the blood pressure, the vasodilation constant is also obtained so as to check whether vascular sclerosis occurs. The method for detecting vascular sclerosis of the present invention can be applied to a blood pressure monitor. Thus users can measure the vasodilation constant and the blood pressure at the same time. As shown in the step S9, the detected vasodilation constant, the systolic pressure and the diastolic pressure can be displayed.

How the arithmetic circuit 19 calculates and obtains the systolic pressure, the diastolic pressure and the vasodilation constant according to the converted processed signal is described in the following details. The signals received by the arithmetic circuit 19 are waveforms of the gradually decreasing of the pressure detected by the pressure sensor 16 and the waveforms are changed due to pulse beat. The arithmetic circuit 19 records the received processed signals and calculates the systolic pressure, the diastolic pressure, average blood pressure and the pulse rate of the user according to the received processed signals. The average blood pressure calculated by the arithmetic circuit 19 is determined by a pressure value of a point on the oscillating waveform that reaches a maximum amplitude. And the systolic pressure is defined as a pressure of a point on the waveform reaching about 50% maximum amplitude appeared before the waveform arrives the maximum amplitude while the diastolic pressure is defined by a point having about 50% maximum amplitude on the waveform after the waveform arrives the maximum amplitude.

According to the vasodilation constant calculated by the arithmetic circuit 19, whether the blood vessels are becoming less elastic is determined. The vasodilation constant that represents an attenuation constant of the waveform signal obtained during deflation of the cuff 12 is given by the following equation:

$$p = p_0 e^{-(\alpha t)}$$

wherein P is a pressure corresponding to descending waveform of the waveform signal; $p_0$ is an initial pressure corresponding to a starting of the descending waveform; e is a constant; α is an attenuation constant (that's the vasodilation constant); t is descending time of a waveform of the waveform signals. In the above equation, the $p_0$ can be a diastolic pressure. That's the pressure corresponding to the waveform of the diastolic pressure not descending from the peak, also the initial pressure. P is the pressure corresponding to the waveform of the diastolic pressure descending from high level. The P, $p_0$, and t are values measured. Thus according to above equation, the attenuation constant α is calculated and obtained. Therefore, the arithmetic circuit 19 of the present invention can get the vasodilation constant according to the systolic pressure.

The vasodilation constant is proportional to the PWV so that the MY of the user is learned by the vasodilation constant. Thus whether user's blood vessels are normal or not can be checked. The calculation of the vasodilation constant mentioned above is by each descending wave of each oscillation waveform during the deflation of the cuff 12 and regression analysis. The arithmetic circuit 19 of the present invention gets the pulse rate by the numbers of the waveforms of the processed signal received.

Figure 3:
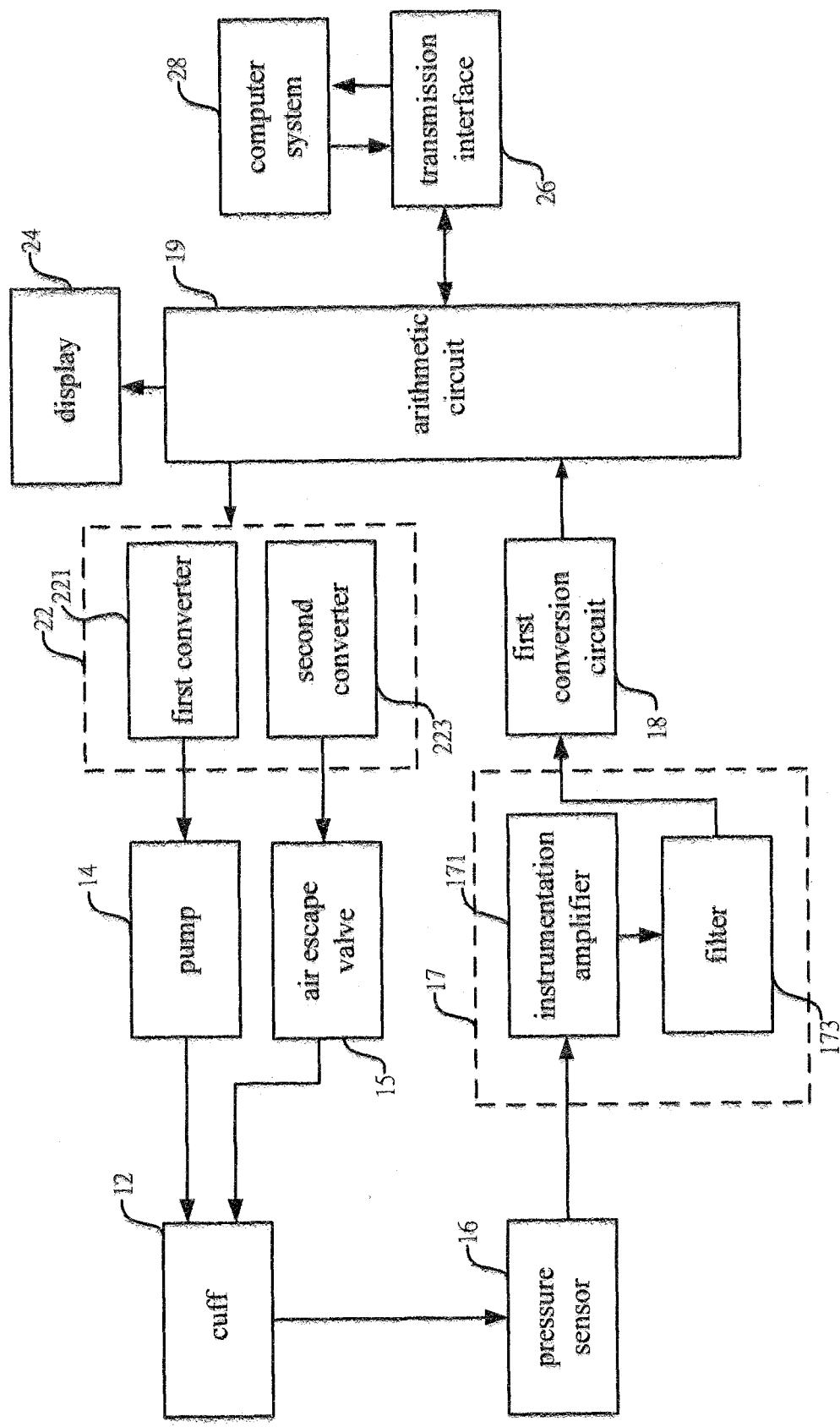
FIG. 3 is a block diagram of another embodiment of a blood pressure monitor that detects vascular sclerosis according to the present invention.

Refer to FIG. 3, a block diagram of another embodiment of a blood pressure monitor related to the present invention is revealed. The difference between this embodiment and the above one is in that this embodiment further includes a transmission interface 26 and a computer system 28. The transmission interface 26 is connected with the arithmetic circuit 19 for sending the processed signal converted by the first conversion circuit 18 while the computer system 28 is coupled with the transmission interface 26 for receiving, processing and analyzing the processed signal from the arithmetic circuit 19. For example, the waveform of the pressure sensing signal generated from the pressure sensor 16 is shown on a display of the computer system 28 or further analysis of the waveform is carried out for other measurement requirements. In a preferred embodiment of the present invention, the transmission interface 26 is a Universal Serial Bus (USB) or other interface with general specifications.

Figure 4:
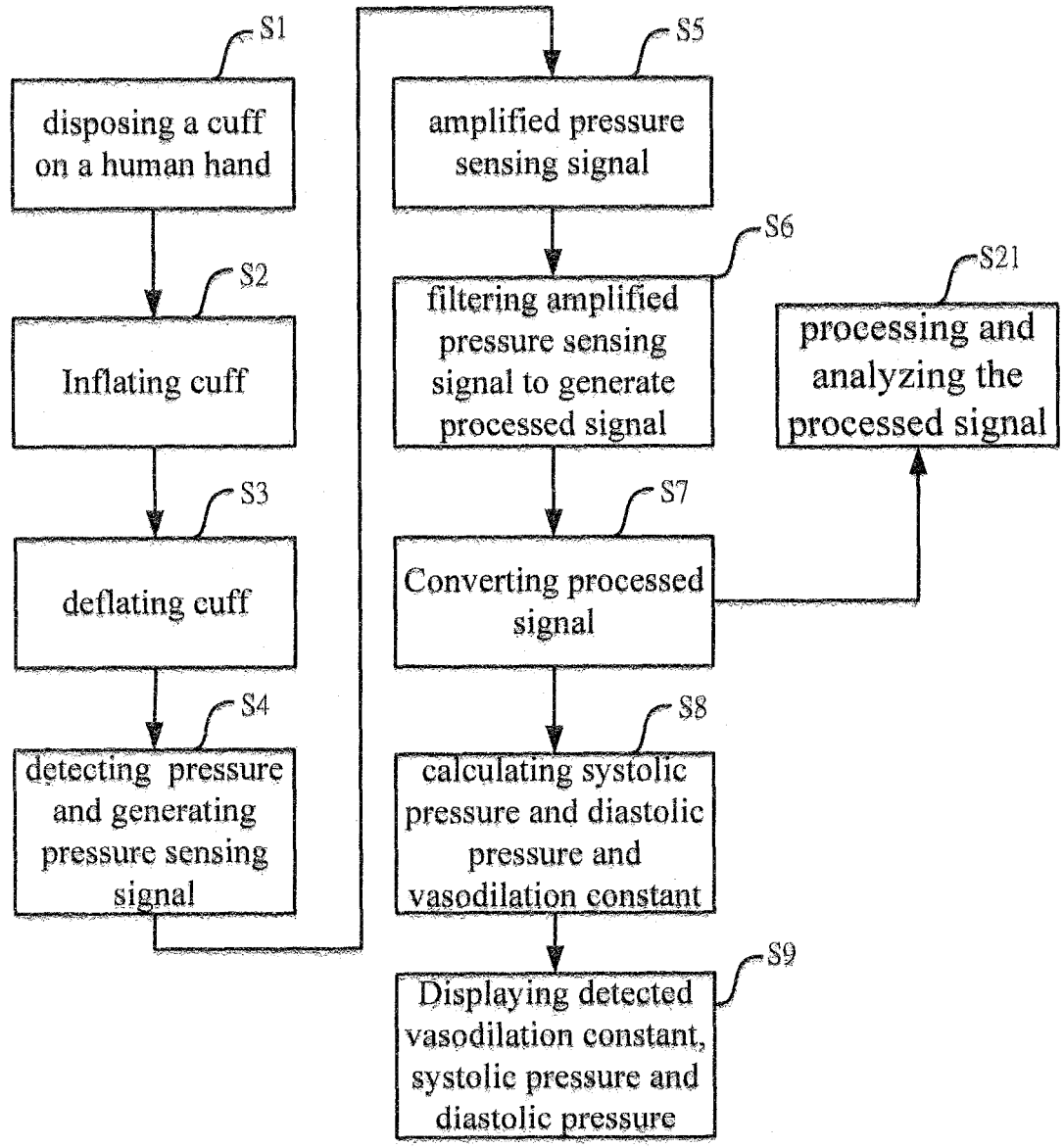
FIG. 4 is a flow chart of another embodiment of a method for detecting vascular sclerosis according to the present invention.

Refer to FIG. 4, another embodiment of the present invention is disclosed. As shown in figure, the difference between this embodiment and the above one is in that this embodiment further includes a step S21, the calculated processed signals are sent to the computer system 28 through the transmission interface 26. The computer system 28 receives, processes and analyzes the processed signals.

In summary, a method for detecting vascular sclerosis according to the present invention is to dispose a cuff on people's hands and inflate the cuff. After completing the inflation, deflate the cuff and measure a pressure of the cuff during the deflation to generate a pressure sensing signal. Then process the pressure sensing signal to generate a processed signal and convert the processed signal. Next calculate a systolic pressure and a diastolic pressure according to the converted processed signal and also obtain a vasodilation constant. Thus the vascular sclerosis is checked according to the vasodilation constant. The method used together with the blood pressure monitor can make the detection become simplified and more prevalent. Therefore people can monitor conditions and changes of their blood vessels whenever they want so as to prevent vascular diseases effectively.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A method for detecting vascular sclerosis comprising the steps of:
    disposing a cuff on a human hand,
    inflating the cuff by an air pump,
    deflating the cuff linearly by the air pump,
    sensing a pressure of the cuff by a pressure sensor, in accordance with oscillating with pulse beats of a human during deflating, and generating a pressure sensing signal by the pressure sensor,
    processing the pressure sensing signal to generate a processed signal by a processing circuit,
    converting the processed signal by a first conversion circuit, and processing the converted processed signal by an arithmetic circuit,
    calculating a systolic pressure and a diastolic pressure of the human by the arithmetic circuit, to get a vasodilation constant in accordance with the converted and processed signal, and checking vascular sclerosis according to the vasodilation constant by the arithmetic circuit,
    wherein the systolic pressure and the diastolic pressure are calculated according to an average blood pressure, the average blood pressure calculated is determined by a pressure value of a point on an oscillating waveform of the converted signal that reaches a maximum amplitude, the systolic pressure is defined as a pressure of a point on the waveform reaching 50% maximum amplitude appeared before the waveform arrives the maximum amplitude while the diastolic pressure is defined by a point having 75% maximum amplitude on the waveform after the waveform arrives the maximum amplitude;
    wherein the vasodilation constant represents an attenuation constant of the waveform signal obtained during deflation of the cuff, and the vasodilation constant is proportional to a pulse wave velocity and is based on the following equation:

$P = p_0 e^{-(\alpha t)}$, wherein

P is a pressure corresponding to descending waveform of the waveform signal; $p_0$ is an initial pressure corresponding to a starting of the descending waveform; e is a constant; α is the attenuation constant which is equal to the vasodilation constant; t is descending time of a waveform of the waveform signals.

2. The method as claimed in claim 1, wherein the step of calculating the vasodilation constant is calculated according to the systolic pressure.

3. The method as claimed in claim 1, wherein the step of processing the pressure sensing signal to generate a processed signal further includes the steps of: amplifying the pressure sensing signal, and filtering the amplified pressure sensing signal to generate the processed signal.

4. The method as claimed in claim 1, wherein in the step of converting the processed signal, the processed signal is converted into a digital signal.

5. The method as claimed in claim 1, wherein the step of calculating the systolic pressure and the diastolic pressure of the human further includes a step of: calculating a pulse rate by the arithmetic circuit.

6. The method as claimed in claim 5, wherein the blood pressure and the pulse rate are displayed.

7. The method as claimed in claim 1, wherein the method further includes the steps of:

transmitting the processed signal to a computer system, and processing and analyzing the processed signal by the computer system.

8. The method as claimed in claim 1, wherein the step of calculating the systolic pressure and the diastolic pressure of the human and calculating the vasodilation constant further includes a step of:

displaying the vasodilation constant, the systolic pressure, and the diastolic pressure.

9. The method as claimed claim 1, wherein the step of inflating the cuff further includes a step of:

generating an inflation control signal to an air pump for control of the air pump to inflate the cuff.

10. The method as claimed in claim 9, wherein the step of generating an inflation control signal to an air pump further includes a step of:

converting the inflation control signal to an analog signal and sending the analog signal to the air pump.

11. The method as claimed in claim 1, wherein the step of deflating the cuff further includes a step of:

generating a deflation control signal to an air escape valve for control of the air escape valve to release air from the cuff.

12. The method as claimed in claim 11, wherein the step of generating an deflation control signal to an air escape valve further includes a step of:

converting the deflation control signal to an analog signal and sending the analog signal to the air escape valve.

13. The method as claimed in claim 1, wherein in the step of inflating the cuff, the cuff is inflated linearly.

\* \* \* \* \*